(12) United States Patent
Allam

(10) Patent No.: US 8,445,549 B2
(45) Date of Patent: *May 21, 2013

(54) SYSTEMS AND PROCESSES FOR PROCESSING HYDROGEN AND CARBON MONOXIDE

(75) Inventor: Rodney J. Allam, Wiltshire (GB)

(73) Assignee: GTLpetrol LLC, New York, NY (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/195,766

(22) Filed: Aug. 1, 2011

(65) Prior Publication Data

US 2012/0059072 A1 Mar. 8, 2012

Related U.S. Application Data

(63) Continuation of application No. 12/488,377, filed on Jun. 19, 2009, now Pat. No. 7,989,509.

(60) Provisional application No. 61/074,571, filed on Jun. 20, 2008.

(51) Int. Cl.
*C07C 27/00* (2006.01)

(52) U.S. Cl.
USPC ............. 518/705; 518/70; 518/702; 518/703; 518/704

(58) Field of Classification Search
USPC .................................................. 518/700–705
See application file for complete search history.

(56) References Cited

U.S. PATENT DOCUMENTS

| | | | |
|---|---|---|---|
| 6,159,395 | A | 12/2000 | Early et al. |
| 6,534,551 | B2 | 3/2003 | Allam et al. |
| 6,669,744 | B2 | 12/2003 | Allam et al. |

FOREIGN PATENT DOCUMENTS

| | | |
|---|---|---|
| JP | 2006-505646 | 2/2006 |
| JP | 2007-527837 | 10/2007 |

OTHER PUBLICATIONS

International Search Report and Written Opinion of the International Searching Authority issued in international application No. PCT/US2009/048021, mailed on Feb. 12, 2010, 8 pages.

*Primary Examiner* — Jafar Parsa

(74) *Attorney, Agent, or Firm* — Fish & Richardson P.C.

(57) ABSTRACT

In various implementations, various feed gas streams which include hydrogen and carbon monoxide may be processed for conversion to product streams. For example, the feed gas stream may be processed using the Fischer-Tropsch process. Unconverted hydrogen and carbon monoxide can be recycled using an off-gas catalytic reformer and a gas turbine exhaust gas heat exchanger that will perform preheating duties.

9 Claims, 1 Drawing Sheet

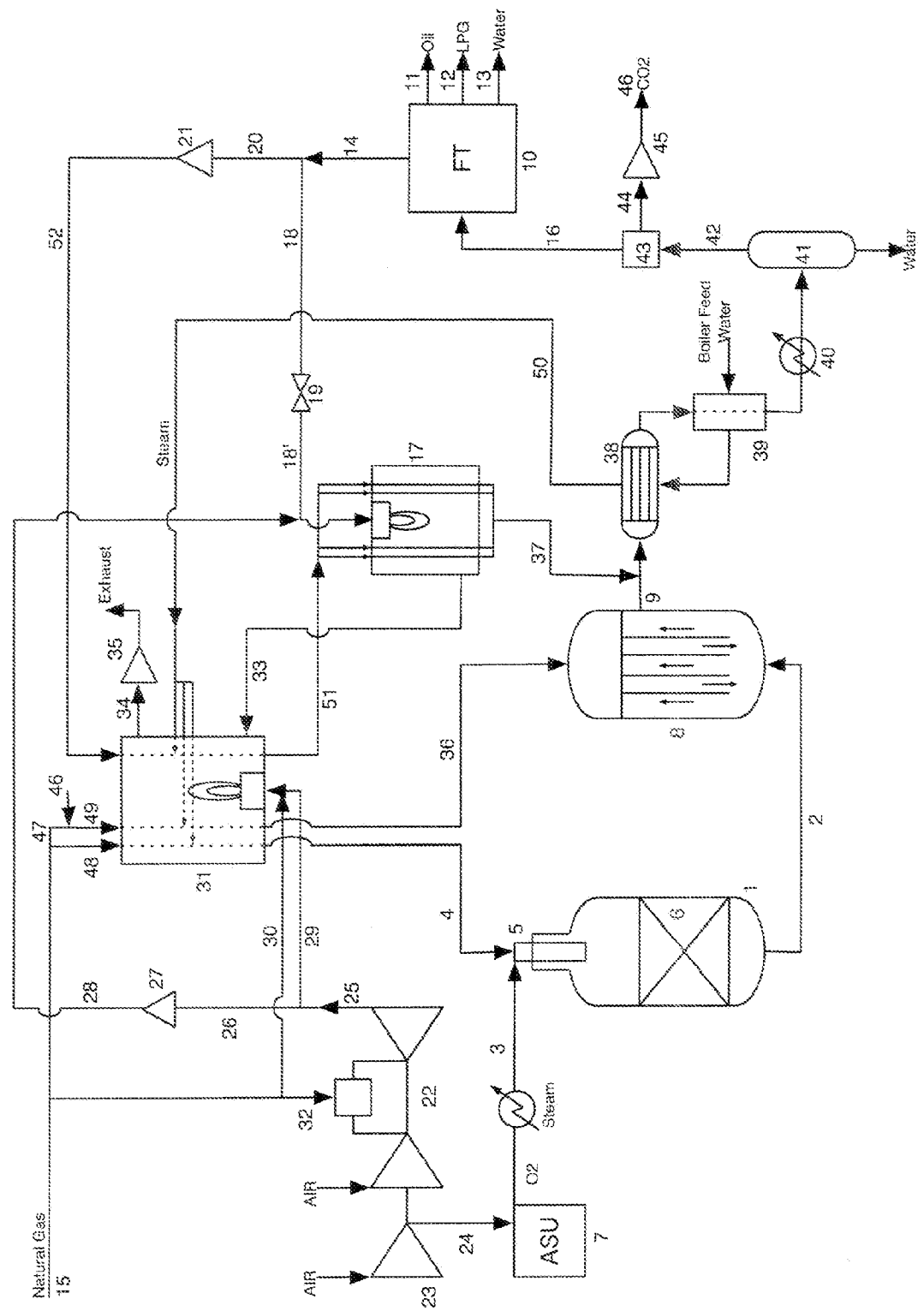

SYSTEMS AND PROCESSES FOR PROCESSING HYDROGEN AND CARBON MONOXIDE

CLAIM OF PRIORITY

This application is a continuation of and claims priority under 35 USC §119(e) to U.S. patent application Ser. No. 12/488,377, filed on Jun. 19, 2009, the entire contents of which are hereby incorporated by reference, which claims priority under 35 USC §119(e) to U.S. Provisional Application No. 61/074,571, filed Jun. 20, 2008, the entire disclosure of which is incorporated herein by reference.

TECHNICAL FIELD

The present disclosure relates to hydrogen and carbon monoxide processing.

BACKGROUND

Hydrocarbon and carbonaceous feedstock can be converted into $H_2$ and CO synthesis gas mixtures with varying ratios of $H_2$ to CO. Feedstock may include coals, natural gas, oil fractions, bitumen and tar-like refinery wastes, pet-coke and various forms of biomass. The synthesis gas mixtures can be converted into valuable hydrocarbons and chemicals using catalytic processes.

SUMMARY

In various implementations, unconverted synthesis gas, bi-product gases and inert gases left after catalytic conversion of synthesis gas into higher value hydrocarbon products and chemicals are converted into additional quantities of synthesis gas to improve the economics of the overall processes.

The conversion processes used to produce the synthesis gas may include partial oxidation, steam reforming, auto-thermal reforming, convective reforming, carbon monoxide shift conversion, and combinations of these processes. In some implementations, processes similar to the processes described in U.S. Pat. Nos. 6,669,744 and 6,534,551 may be used to produce $H_2$ and CO synthesis gas mixtures with extremely high efficiency. This defines a process for the production of synthesis gas from a hydrocarbon fuel and steam and oxygen gas wherein at least part of any steam requirement is provided by heat exchange against an exhaust gas from a gas turbine driving an air compressor in an air separation unit supplying at least part of the oxygen requirement for the synthesis gas generation process. An important feature of this process is the integration of a primary synthesis gas production unit, such as a partial oxidation reactor (POX) or an auto-thermal reactor (ATR) with a convectively heated steam/hydrocarbon catalytic reformer (GHR), so that the combined synthesis gas product stream can be used to provide the heat required for the endothermic steam/hydrocarbon reforming reactions taking place in the GHR tubes. The combination maximizes the synthesis gas production from a given quantity of hydrocarbon feed and provides a very compact and low cost synthesis gas generation process by eliminating the normal large quantity of high pressure steam production generally used for power production in steam turbines and substituting much cheaper high efficiency gas turbines thermally linked to the synthesis gas generation process.

Examples of the products of catalytic conversion of synthesis gas include Fischer-Tropsch hydrocarbons, methanol, oxo-alcohols, and methane. In some implementations, these catalytic processes may not result in complete conversion of the feed synthesis gas into the desired products. Since there will be some unconverted synthesis gas, the unconverted synthesis gas may be recycled back to the inlet of the catalytic conversion process. The unconverted synthesis gas may be a mixed stream, often including other compounds such as inert gases (e.g., argon and nitrogen) and carbon dioxide. These other compounds may arise either from mixture with oxygen used in partial oxidation or auto thermal reforming to produce the synthesis gas or the carbonaceous or hydrocarbon feedstock used. In addition, side reactions in the catalytic synthesis gas conversion processes may produce bi-products such as $CH_4$, $CO_2$ and possibly $C_3$ and $C_4$ components that may be in the mixed stream with the unconverted synthesis gas.

To improve the process economics (e.g., by maximizing conversion efficiency of feedstocks to final products), one, more, or none of the following features may be implemented. The unconverted synthesis gas may be used with the associated inert components and other bi-products, and may be recycled back to the feed point of the synthesis gas conversion process.

In some implementations, the unconverted gas recycle system may be used with various synthesis gas generation processes, as described below or as described in U.S. Pat. Nos. 6,669,744 and 6,534,551. As described in U.S. Pat. Nos. 6,669,744 and 6,534,551, at least part of any steam requirement for a process for the production of synthesis gas is provided by heat exchange with exhaust gas from a gas turbine driving an air separation unit, which supplies at least part of any oxygen requirement for the synthesis gas production. The described processes may be used when the synthesis gas is used in methanol syntheses or Fischer-Tropsch processes.

In some implementations, carbon dioxide and other inert gases, such as argon and nitrogen, may be separated from the unconverted synthesis gas to reduce the effect on the synthesis gas conversion process and/or to prevent a build-up of inert gas concentration in the catalytic conversion process. Buildup of inert gases in the catalytic conversion process may affect the equilibrium of the reactions and, thus, reduce conversion rates. In some implementations, by using the final unconverted synthesis gas, inert gases and by-products and steam as feed to a catalytic reformer process (e.g., off-gas catalytic steam/hydrocarbon reformer), more synthesis gas may be produced for the synthesis gas conversion process. Part of the off gas containing inerts may be used as combustion fuel gas to heat the catalytic reformer and this will limit the buildup of inerts in the system.

In some implementations, the system may include an off-gas catalytic reformer integrated with a gas turbine exhaust gas heat exchanger. Use of the off-gas catalytic reformer integrated with a gas turbine exhaust gas heat exchanger may reduce the need for and/or eliminate the entire reformer furnace exhaust gas convective heat exchange system, which is an integral part of typical conventional catalytic steam/hydrocarbon reforming processes that produce $H_2$+CO synthesis gas. This may be implemented by ducting a portion of or the entire reformer furnace exhaust gas into the base of the gas turbine exhaust gas fired heat exchanger. In some implementations, the ducting may be at or proximate a point above the burner section. Use of the integrated off-gas catalytic reformer with a gas turbine exhaust gas heat exchanger may allow the preheating duties (e.g., for the entire system) to be performed in this one unit.

In some implementations, part of the exhaust gas from the gas turbine may be used as combustion air for the off-gas catalytic reformer furnace burners. The exhaust gas may be approximately 400° C. to 500° C. and it may require compression to a pressure suitable for the burners in the catalytic reformer furnace. Use of at least a portion of the exhaust gas as combustion air may reduce the quantity of fuel needed for heating the reformer furnace. Reducing the amount of fuel needed for heating may reduce processing costs. Alternatively, the combustion air may be taken from a suitable interstage position in the $O_2$ plant air compressor.

In some implementations, the entire product synthesis gas cooling train associated with the off-gas catalytic reformer, normally associated with a steam/hydrocarbon catalytic reformer, may be removed (e.g., the need for the product synthesis gas cooling train may be removed) or eliminated from the system. Instead, the synthesis gas leaving the tubes at the outlet of the reformer furnace may be fed into the inlet of the waste heat boiler, which takes the entire synthesis gas stream leaving the GHR shell side. This may eliminate or reduce the need for a second waste heat boiler, feed-water pre-heater, water cooled synthesis-gas cooler, water separator and/or a separate steam system. Eliminating these components may reduce processing costs (e.g., by utilizing heat generation within the process) and/or reduce system costs (e.g., by reducing the cost of components needed for the system and/or by removing maintenance costs associated with the eliminated components).

These features may reduce the capital cost and/or maximize the efficiency of the additional off-gas catalytic reformer. These features may be used in combination with the basic technology disclosed in U.S. Pat. Nos. 6,669,744 and 6,534,551, which integrate synthesis gas generation with a gas turbine power unit with waste heat recovery.

In some implementations, $H_2$ and CO production from the combined primary synthesis gas generation reactor, POX or ATR may be increased and/or maximized. The primary synthesis gas generation reactor may be integrated with the GHR. $H_2$ and CO production may be increased by recycling separated $CO_2$ from the total synthesis gas production to the primary synthesis gas generation reactor and/or the GHR feed gas streams giving a higher CO to $H_2$ ratio in the primary synthesis gas, and by balancing this with the higher $H_2$ to CO ratio from the off-gas catalytic reformer to increase the production of $H_2$ and CO from the total synthesis gas generation system and achieve the required $H_2$ to CO ratio in the synthesis gas feed to the catalytic synthesis gas conversion process. In some implementations, a $CO_2$ separation unit may be used. The $CO_2$ separation unit may be at least partially based on solvent scrubbing of the combined synthesis gas feed streams entering the catalytic conversion of synthesis gas process. This separated $CO_2$ may be recycled (e.g., up to 100% recycle) back to the primary synthesis gas generation reactor and/or the GHR.

The details of one or more implementations are set forth in the accompanying drawings and the description below. Other features, objects, and advantages of the implementations will be apparent from the description and drawings.

DESCRIPTION OF DRAWINGS

FIG. 1 illustrates an example processing system.
Like reference symbols in the various drawings indicate like elements.

DETAILED DESCRIPTION

In various implementations, various feed gas streams which include hydrogen and carbon monoxide, may be processed for catalytic conversion to product streams. As an example, the feed gas stream may be processed using the Fischer-Tropsch process. Unconverted hydrogen and carbon monoxide, together with other components such as inerts, hydrocarbons and $CO_2$, can be recycled by conversion primarily to $H_2$+CO using an off-gas catalytic steam/hydrocarbon reformer, and a gas turbine exhaust gas heat exchanger may perform preheating duties. By utilizing heat generated during the process to preheat various portions, costs may be reduced.

FIG. 1 illustrates an example processing system for the processing of $H_2$ and CO. As illustrated, an autothermal reforming reactor (ATR) (unit 1) produces a product stream that includes a CO and $H_2$ mixture (stream 2) plus unconverted $CH_4$, steam and $CO_2$. As an example, the product stream (stream 2) may be at approximately 37 bar and approximately 1025° C. $O_2$ is fed to the ATR (unit 1) at approximately 270° (stream 3). The $O_2$ may be produced in an air separation unit (ASU) (unit 7). A mixture of natural gas and steam (e.g., at approximately 550° C.) (stream 4) may also be fed to the burner (unit 5) of the ATR (unit 1). The mixture of natural gas and steam (stream 4) may be a portion of a product stream from a first heater (unit 31). The ATR (unit 1) may also include a catalyst bed (unit 6) for reforming the gas mixture produced in the burner (unit 5).

The Gas Heated Reformer (GHR) (unit 8) may also be fed with a mixture of natural gas and steam (e.g., at approximately 550° C.) (stream 36). The mixture of natural gas and steam may flow downwards through catalyst in the GHR (e.g., catalyst filled vertical open ended tubes) (unit 8) and may exit the GHR mainly as a mixture of $H_2$ and CO with some unconverted $CH_4$, $CO_2$, steam and inerts. This gas may exit at approximately 900° C. This gas may also mix with the product gas of the ATR (stream 2) in the GHR (unit 8). The combined stream (e.g., gas exiting the catalyst tubes mixed with the product stream from the ATR) flows upwards through the shell side of the GHR (unit 8) and/or may provide the heat required for the steam/hydrocarbon reforming reactions. The product gas stream (stream 9) may exit the GHR at approximately 600° C. and approximately 36 bar. Other arrangements, such as POX+GHR, are also possible.

A Fischer-Tropsch multistage reactor with associated hydro-treater (FT) (unit 10) may process a $H_2$ and CO feed stream (stream 16) to produce oil (stream 11), liquefied petroleum gas (LPG) (stream 12) and water (stream 13). The $H_2$ and CO feed stream may be at approximately at 35 bar and 30° C. The unconverted gas mixture (stream 14) produced by the FT reactor after product separation may include $H_2$, CO, $CH_4$, inert gases such as $N_2$ and Ar, and trace quantities of $C_2$, $C_3$ and $C_4$. The unconverted gas mixture (stream 14) may be at approximately 30 bar. The compounds in the unconverted gas mixture may include components from the oxygen (stream 3) and the natural gas feed (stream 15). The unconverted gas stream (stream 14) or "off-gas" generally contains approximately 5% to 10% of the $H_2$ and CO present in the feed stream 16 to the FT reactor (unit 10).

Stream 14 may be converted to $H_2$ and CO synthesis gas in the steam/hydrocarbon off-gas catalytic reformer 17. The unconverted gas stream 14 is divided (e.g., after exiting the FT reactor) into at least two streams, stream 18 and stream 20. In some implementations, stream 14 may be divided unequally into the at least two streams (e.g., stream 20 may be larger, by volume or weight, than stream 18). The pressure of stream 18 is reduced to approximately 1.3 bar in valve 19 (e.g., the valve allows the stream to be expanded) to produce stream 18'. Stream 18', which includes part of the unconverted gas mixture at a lower pressure than the exit stream from the FT reactor, is used as fuel gas for heating the furnace of the steam/hydrocarbon off-gas reformer (unit 17). Thus, separate or additional fuel may not be necessary to operate the reformer (unit 17), which may reduce costs.

Stream 20 may be compressed to approximately 38 bar in compressor 21 to produce stream 52. Stream 52 may be provided as a portion of the feed to heater 31. The feed stream (stream 51) to the steam/hydrocarbon off-gas catalytic reformer (unit 17) may be produced in the heater 31 by heating stream 52 in the heater 31; mixing steam, as required for the reformer, from stream 50; and superheating the mixture. Stream 51, which is provided as feed to the steam/hydrocarbon off-gas catalytic reformer (unit 17), may be at approximately 550° C.

A gas turbine (unit 22) drives an air compressor (unit 23) which may provide the feed air stream 24 to the ASU (unit 7). A portion of the natural gas feedstock (stream 15) may be provided to the gas turbine (unit 22) as fuel (stream 32). The gas turbine exhaust (stream 25) may be at approximately 450° C. The gas turbine exhaust (stream 25) may be divided into at least two streams, stream 26 and stream 29, for example, as it exits the gas turbine (unit 22). Stream 26 may be compressed (e.g., to approximately 1.2 bar). The stream 26 may be compressed using, for example, a blower (unit 27). The stream exiting the blower is provided as the combustion air stream (stream 28) for the furnace of the steam/hydrocarbon off-gas catalytic reformer (unit 17). Alternatively, stream 26 may be taken from an intermediate pressure interstate position of the ASU feed air compressor (unit 23)

Stream 29 is further heated by the combustion of the natural gas stream 30 to produce heating gas for the heater (unit 31). The heater (unit 31) may be able to perform the preheating duties for all the natural gas and steam requirements of the whole system. In some implementations, the heater may perform a portion (e.g., a majority) of the preheating duties. For example, the natural gas stream (stream 30) may be a portion of the natural gas feed stock (stream 15).

The exit combustion product stream (stream 33) from the furnace of the off-gas catalytic reformer (unit 17) may be at approximately 700° C. to 1100° C. and/or may enter proximate the base of the heater (unit 31). The exit stream (stream 33) may mix with the hot gas exiting the burner area of the heater (unit 31) and be cooled (e.g., the mixed stream may have an exit temperature of approximately 200° C.). In some implementations, the exit stream may be cooled because of the heating duty of the stream. The resulting cooled gas stream (stream 34) may then exit the heater and may be vented to the atmosphere using, for example, an induced draft fan (unit 35). The induced draft fan (unit 35) may ensure that the exhaust gas pressure of the gas turbine stream (stream 25) is adequate for power generation in the gas turbine (unit 22).

The $H_2$ and CO synthesis gas (stream 37) produced in the off-gas catalytic reformer (unit 17) may exit at a temperature from approximately 750° C. to 900° C. and may be mixed with the synthesis gas product stream (stream 9) exiting the shell side of the GHR (unit 8). The combined synthesis gas stream may cool in the waste heat boiler (unit 38) and the feed water heater (unit 39). At least a portion of this combined synthesis gas stream may then be fed into a water cooler (unit 40). The exit stream from the water cooler (unit 40) may then be fed into a water separator (unit 41), which removes at least a portion of the condensed water from the combined synthesis gas stream. $CO_2$ may be removed from the cooled synthesis gas stream 42 using, for example, a solvent scrubber (unit 43). Regeneration heat for the solvent $CO_2$ scrubber (unit 43) is provided by the low pressure steam generated as a by-product in the FT reactor (unit 10). The separated $CO_2$ (stream 44) may be compressed (e.g., to approximately 38 bar) in a compressor (unit 45) to produce a $CO_2$ stream (stream 46). At least a portion of the produced stream of $CO_2$ may then be mixed with the desulphurised natural gas feed stream (stream 47) to the heater (unit 31) to provide the feed stream (stream 49) for the GHR (unit 8). The ATR desulphurised natural gas feed stream (stream 48) and the mixed GHR feed stream (stream 49) may pass through a first stage of heating in the heater (unit 31). The streams (streams 48, 49) are then mixed with steam, as required for the process, from stream 50. The steam may be saturated steam at approximately 38 bar which was produced in the waste heat boiler (unit 38). The combined streams are then further heated to an exit temperature of approximately 550° C. in the heater (unit 31) to produce exit streams (streams 4 and 36).

An effect of the process integration may be to allow the FT off-gas, which has a very large amount of $CH_4$ content, to be used to produce up to about 25% of the total $H_2$ and CO required by the FT process. This may be performed in a way that increases or maximizes efficiency. The ratio of CO to $H_2$ in the combined feed stream (stream 16) entering the FT reactor system (unit 10) can be adjusted by varying the quantity of $CO_2$ (stream 46) fed to the GHR (unit 8) to produce a high CO to $H_2$ ratio in stream 9 compensated by a low CO to $H_2$ ratio in stream 37. This maximizes the quantity of by-product $CO_2$ recycled for use in the process and minimizes $CO_2$ emission to atmosphere. In addition, the peripheral equipment required by a conventional steam/hydrocarbon reformer may be substantially eliminated or reduced. This may be performed at very low capital cost increment. The inert gases (e.g., $N_2$, Ar, $CO_2$) in stream 18 may be vented to atmosphere through heater 31. This may inhibit the concentration of inert gases from building up, which may be caused otherwise when synthesis gas is recycled through the system. When the concentration of inert gases increases beyond a specified concentration, the process efficiency may be decreased.

Although a specific implementation of the system is described above, various components may be added, deleted, and/or modified. In addition, the various temperatures and/or concentrations are described for exemplary purposes. Temperatures and/or concentrations may vary as appropriate. In addition, although the above process is described in terms of an FT process, similar systems may be used in conjunction with methanol synthesis.

A number of implementations have been described. Nevertheless, it will be understood that various modifications may be made without departing from the spirit and scope of the implementations. Accordingly, other implementations are within the scope of this application.

It is to be understood the implementations are not limited to particular systems or processes described which may, of course, vary. It is also to be understood that the terminology used herein is for the purpose of describing particular implementations only, and is not intended to be limiting. As used in this specification, the singular forms "a", "an" and "the" include plural referents unless the content clearly indicates otherwise. Thus, for example, reference to "a reactor" includes a combination of two or more reactors and reference to "a feedstock" includes different types of feedstocks.

What is claimed is:
1. A process for producing higher molecular weight hydrocarbon compounds and/or oxygenates from a hydrocarbon gas comprising methane, said process comprising:
　　generating an initial synthesis gas ("syngas") stream comprising carbon monoxide and hydrogen in a two-stage process by reaction of hydrocarbon gas comprising methane, steam and oxygen;

generating the oxygen in an air separation plant having an air compressor driven by a gas turbine;

combusting a fuel gas in exhaust from the gas turbine in a fired heater to provide at least a portion of a heat duty for preheating feed streams to synthesis gas production units;

catalytically converting synthesis gas to at least one of hydrocarbons or oxygenates in a process unit, at least a portion of the initial syngas stream is provided as feed gas to the process unit;

separating off-gas from the process unit, the off-gas including unreacted syngas from the feed gas, inerts, reaction products, $CO_2$ and water vapor; and generating additional synthesis gas in a catalytic steam/hydrocarbon reformer using the off-gas, a first part of the off-gas is used to provide at least a portion of the fuel gas for the reformer heating, and a second portion is used to provide at least a portion of the feed to the catalytic reformer mixed with steam.

2. The method of claim 1 further comprising using at least a portion of hot exhaust from the gas turbine compressed as combustion air for the off-gas catalytic reformer.

3. The method of claim 1 further comprising using at least a portion of air taken from the air separation unit air compressor at a suitable interstage point before an intercooler having a specified pressure for burners as combustion air for the off-gas catalytic reformer.

4. The method of claim 1, wherein generating the initial syngas stream comprises:

reacting hydrocarbon-containing fuel with an oxidant gas comprising molecular oxygen and steam in a first autothermal catalytic reformer to produce a syngas product; and endothermically reforming hydrocarbon-containing fuel gas with steam over a catalyst in a heat exchange reformer to produce a heat exchange-reformed syngas product, wherein at least a portion of the heat used in the generation of said heat exchange-reformed syngas product is obtained by recovering heat from the syngas product leaving the autothermal catalytic reformer.

5. The method of claim 1, wherein generating the initial syngas stream comprises:

exothermically reacting hydrocarbon-containing fuel with an oxidant gas comprising molecular oxygen in a first reactor to produce an exothermically-generated syngas product; and endothermically reforming hydrocarbon-containing fuel gas with steam over a catalyst in a heat exchange reformer to produce a heat exchange-reformed syngas product, wherein at least a portion of the heat used in the generation of said heat exchange-reformed syngas product is obtained by recovering heat from the exothermically-generated syngas product.

6. The method of claim 1, the two-stage process comprises a Fischer-Tropsch system.

7. The method of claim 1, the two-stage process comprises a methanol system.

8. The method of claim 1, further comprising separating $CO_2$ from feed gas stream entering the two-stage process and recycling at least a portion of compressed $CO_2$ to the initial syngas generation system to form an initial syngas having a CO to $H_2$ ratio higher than that required by the catalytic syngas conversion process and simultaneously operating the off-gas reformer to produce a syngas product having a low CO to $H_2$ ratio such that the mixed streams have the required CO to $H_2$ ratio for the catalytic syngas conversion process and the quantity of $CO_2$ recycled is maximized.

9. The method of claim 1, further comprising adding additional fresh hydrocarbon feed to the off-gas catalytic reformer to allow additional $H_2$ production to ensure all the available $CO_2$ separated from the feed syngas to the syngas catalytic conversion process is recycled to the initial syngas production system.

* * * * *